United States Patent [19]

Andersen et al.

[11] Patent Number: 4,863,475
[45] Date of Patent: Sep. 5, 1989

[54] IMPLANT AND METHOD FOR PRODUCTION THEREOF

[75] Inventors: Phillip J. Andersen, Silver Lake; Jack E. Parr, North Webster, both of Ind.

[73] Assignee: Zimmer, Inc., Warsaw, Ind.

[21] Appl. No.: 645,890

[22] Filed: Aug. 31, 1984

[51] Int. Cl.$^4$ .............................................. A61F 2/28
[52] U.S. Cl. .................................... 623/16; 623/901; 623/66
[58] Field of Search ............... 427/2, 214; 3/1.9, 1.81, 3/1.811, 1.812, 1.913; 128/92 C, 92 CA, 92 G, 335

[56] References Cited

U.S. PATENT DOCUMENTS

| 4,146,936 | 4/1979 | Aoyagi et al. | 128/92 YO |
| 4,309,488 | 1/1982 | Heide et al. | 623/16 |
| 4,322,398 | 3/1982 | Reiner | 3/1.9 |
| 4,330,891 | 5/1982 | Branemark et al. | 128/92 C |
| 4,366,183 | 12/1982 | Ghommidh et al. | 3/1.9 |
| 4,483,678 | 11/1984 | Nishio et al. | 128/92 C |
| 4,495,664 | 1/1985 | Blanquaert | 128/92 C |

Primary Examiner—Richard J. Apley
Assistant Examiner—David J. Isabella
Attorney, Agent, or Firm—Paul David Schoenle

[57] ABSTRACT

An implantable prosthesis including a base member, such as the stem of a hip joint prosthesis, having a porous region on its surface, and the region of porosity being coated with a bioabsorbable material, such as α-tricalcium phosphate, which enhances permanent bone ingrowth into the region. A method of manufacture of the prosthesis includes the steps of providing a coating material and applying the material to at least a portion of the porous surface of the base member, while providing energy sufficient to transform the material to a state in which it is bioabsorbable. In the preferred embodiment the material is plasma sprayed onto the porous surface of the base member.

2 Claims, 2 Drawing Sheets

IMPLANT AND METHOD FOR PRODUCTION THEREOF

BACKGROUND OF THE INVENTION

1. Field of the Invention

The invention in general relates to medical prostheses for implantation in a body, and more particularly to prostheses which are fixed within the body by means of bone ingrowth into the prostheses.

2. Description of the Prior Art

Medical devices such as bone plates, nails, pins, screws, and joint prostheses have been commonly implanted into the skeletal structure of humans and animals for many years to join the parts of a fractured bone or to replace missing or damaged skeletal parts. Often it is intended that these parts become a permanent part of the body. In such cases it is important that the parts be strongly and permanently fixed to the skeletal bone structure.

It has been known for more than 10 years that strong permanent fixation can be obtained by the use of a porous surface on the whole or a portion of the part, provided that the mean pore size exceeds about 50 micrometers. However, the older methods of bone fixation, primarily fixation by friction fit or with methyl methacrylate bone cement, still are the most predominately used methods of fixation, in spite of the fact that the loosening of friction fitted and cement bonded prostheses parts over time remains a significant medical problem. This is because in order to obtain good fixation by means of bone ingrowth, the patient must refrain from applying force or loading on the skeletal implant until the bone growth occurs, whereas in the case of friction fit or cement bonding skeletal loading can take place almost immediately.

In this disclosure, the words bioabsorbable and resorable mean that the substance to which the term is applied is broken down, absorbed, or otherwise removed by the host body chemistry in amounts sufficient to alter the physical structure of the portion of the device which is bioabsorbable within a time period less than the period it takes for bones to fully mend. It is understood that all materials, even steel, are slightly absorbed by the body chemistry, however, such slight absorbtions, which do not alter the physical structure of the bioabsorbable device over the period of bone healing, are not included in the terms bioabsorbable and resorbable. it is also understood that although a material is bioabsorbable, some small amount of it may remain in the body for longer periods.

One method shown to encourage earlier bone ingrowth into porous surfaces of implants is the coating of porous metal fibers with hydroxyapatite by dipping the fiber into a water slurry of hydroxyapatite and drying. Hydroxyapatite is not generally considered to be resorbable in the human body. It was found that the hydroxyapatite encourages more rapid ingrowth of bone into the porous metal surfaces for a time period of up to four weeks after implant, but that the effect was short term, in that the amount of bony tissue within the pores declined after the four week period, P. Ducheyne, et al. "Effect of Hydroxyapatite Impregnation on Skeletal Bonding of Porous Coated Implants" *Journal of Biomedical Materials Research*, Vol. 14, 225-237 (1980). In addition to the fact that the increased ingrowth was not permanent, it has been found that the hydroxyapatite encourages fibrous rather than bony tissue growth at the fixation site over long time periods, which can result in loosening of the prostheses. Further, the hydroxyapatite coating in the Ducheyne et al. article is relatively fragile and can be easily broken under normal handling for commercial products, and thus it does not lend itself to widespread commercial use.

The following United States patents relate to the aspects of the present invention as indicated. U.S. Pat. No. 3,605,123 issued to H. Hahn discloses the plasma spraying of a metal porous surface onto a prosthesis. U.S. Pat. Nos. 3,892,648 and 3,892,649 issued to David C. Phillips et al. disclose the electrodeposition of bone and collagen on implants or into a plastic mesh on implants to stimulate bone attachment to the implant.

U.S. Pat. No. 3,919,723 discloses the embedding of calcium and phosphate atoms in the surface of a ceramic implant by heating the implant and embedding it in a melt of calcium phosphate material. It is specifically indicated that temperatures should not be used which decompose one of the materials. calcium phosphate material decomposes at higher temperatures. This decomposition at higher temperatures is characteristic of calcium phosphate materials. See E. Hayek and H. Newesely, *Inorganic Synthesis* 7 (1963) 63.

U.S. Pat. No. 4,202,055 issued to Reiner et al. discloses the combining of a bioabsorbable, bioactive calcium phosphate with a polymer on the surface of a prosthesis, to create bone ingrowth into the polymer. U.S. Pat. Nos. 4,365,357 and 4,373,217 issued to Draenert disclose the combining of the absorbable tricalcium phosphate material with bone cement to create bone growth into the cement. Each of the above three patents involve the incorporation of the absorbable material into the material out of which the surface is composed, and contemplate that the porous surface is created by absorption of the absorbable material thereby leaving pores in the surface in the position of the vacancy created by the absorption of the absorbable material. None of these patents suggest the coating of an already porous surface with an absorbable material in order to enhance bone growth.

U.S. Pat. No. 4,338,926 issued to Kummer et al. discloses the addition of a bioabsorbable layer 0.1 to 1 mm thick on an implant surface; the intention is to create loosening of the implant as the material is absorbed. The prosthesis on which the absorbable layer is placed is specifically non-porous, since bone ingrowth is to be discouraged.

SUMMARY OF THE INVENTION

It is an object of the invention to provide a prosthesis that results in rapid and permanent bone ingrowth into a porous surface thereby providing early, strong, and permanent fixation of the implant into the skeletal structure.

It is a further object of the invention to provide a prosthesis, and a method of manufacturing the prosthesis, which overcome the disadvantages of the prior art prostheses that were intended to be permanently affixed to bone.

The invention provides a part for attachment to skeletal bone comprising a base member having a porous region on the surface thereof, and a bioabsorbable coating on at least a portion of the region of porosity, which material enhances permanent bone ingrowth into the region of porosity.

It has been found that the base member does not loosen as the porous surface coating is absorbed as suggested in the prior art. Rather, the absorbable material, in a manner not entirely understood, encourages faster and stronger bone ingrowth into the porous surface which it covers. Further, the ingrowth stimulated remains permanently, and is a bony material, rather than a fibrous, weak tissue as has been found to occur with hydroxyapatite coatings.

The invention provides a method of manufacturing a prosthetic part for use as a body implant comprising the steps of: providing a base member having a porous surface region on which bone attachment is desired; providing a material which after heating to a high temperature cools to a state in which it is bioabsorbable; heating the material to a temperature greater than 1350° C. and applying it to at least a portion of the porous surface region of the base member. Preferably the material includes at least one substance selected from the group consisting of hydroxyapatite and β-tricalcium phosphate and upon heating and cooling the material transforms to primarily α-tricalcium phosphate. It has been found that the high temperature application of the coating results in a coating that is both bioabsorbable and more adherent than the prior art coatings. It has been found that the coating is sufficiently adherent to enable the parts to be boxed, sterilized, and handled generally for implanting purposes without loosening from the base member.

Thus, the invention has solved a problem long recognized in the prior art. Numerous other aspects, features, objects, and advantages of the invention will now become apparent from the following detailed description when read in conjunction with the accompanying drawings, in which:

DESCRIPTION OF THE PREFERRED EMBODIMENT

Figure 1:
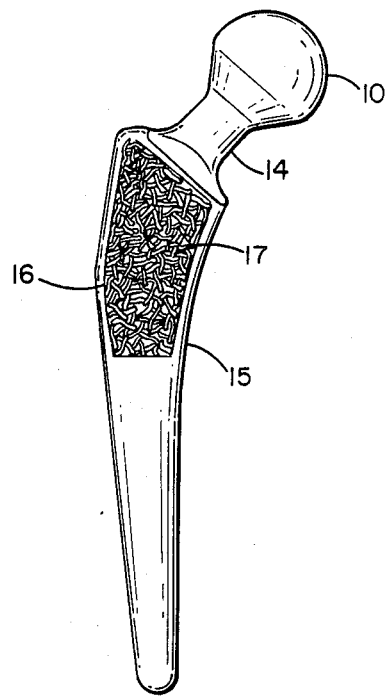
FIG. 1 is a side view of a body implant according to one embodiment of the invention.

Referring to FIG. 1, there is shown a prosthetic part intended to be used as a body implant. The particular prosthetic part shown is a hip prosthesis. Such prostheses conventionally include a smooth, ball-shaped head 10 which forms one surface of the hip joint, and which is intended to rotate within a socket in the hip, a neck 14 and a base member or stem 15. The stem 15 is intended for anchoring within the femur of the human or animal patient. In order to enhance the fixation of the stem 15 within the femur, a region 16 of the surface of stem 15 is porous. In the embodiment of FIG. 1, the porous region 16 of the stem comprises a mat composed of compressed short metal fibers, such as described in U.S. Pat. No. 3,906,550 issued to William Rostoker and Jorge Galante. According to the invention, the metal fiber mesh 17 is coated with a bioabsorbable material as will be discussed in more detail below.

Figure 2:
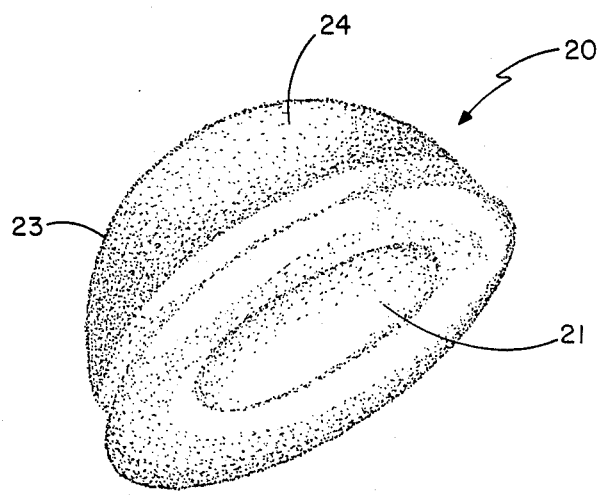
FIG. 2 shows a perspective view of another embodiment of the invention.

FIG. 2 shows a second exemplary embodiment of the invention. The part 20 intended to be implanted is an acetabular hip prosthesis, commonly referred to as a hip cup. The hip cup 20 includes a smooth, spherical surface 21, which forms the other one of the surfaces of a hip joint and which is intended to receive the spherical surface 10 of the prosthesis of FIG. 1. The external surface 23 of the hip cup 20 is intended to be implanted within the acetabulum and is covered with a porous metal surface layer 24 by the process of plasma spraying. The plasma spraying process is described in U.S. Pat. No. 3,605,123 issued to H. Hahn. According to the invention the porous layer 24 includes a bioabsorbable material on at least a portion of its surface, which material enhances the permanent bone growth into the region of porosity. The coating will be described in further detail below.

Another commonly used porous coating with which the invention may be incorporated is a sintered coating of metal particles.

The above types of porous surfaces are intended only as examples, and it should be understood that any of the various types of porous surfaces used for fixation of parts implanted in the body may be incorporated in the invention.

Figure 3:
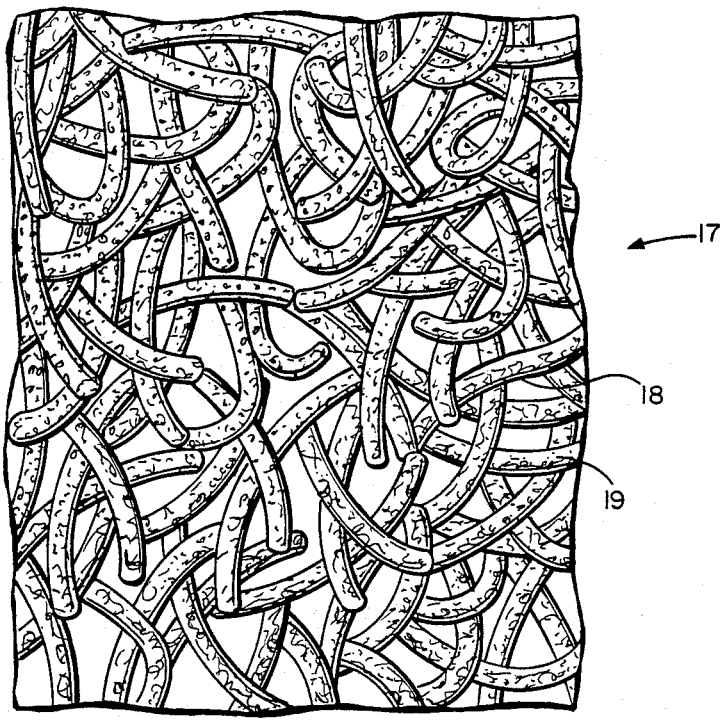
FIG. 3 shows a draftsman's rendering of an actual photograph of a coated porous surface of the type employed in the embodiment of FIG. 1 magnified about 20 times.

Turning now to FIG. 3, a porous surface mesh, such as mat 17, is shown magnified approximately 20 times. The mesh 17 is composed of short metal fibers 18 compressed together, and coated with a bioabsorbable material 19 which in the embodiment shown is primarily α-tricalcium phosphate.

Figure 4:
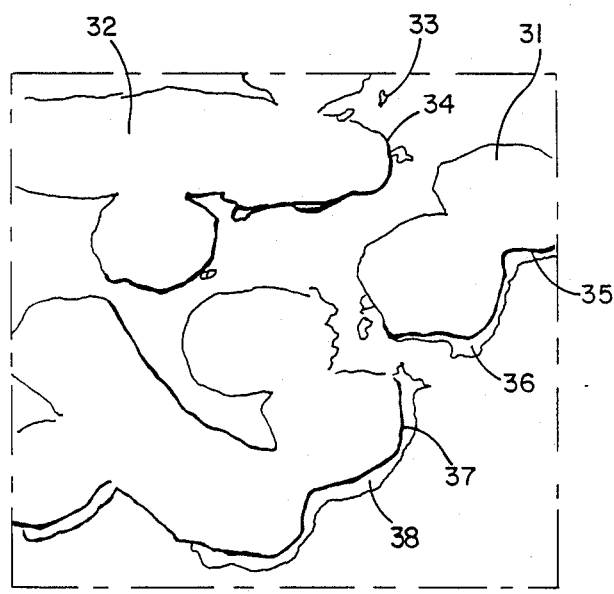
FIG. 4 is a draftsman's rendering of an actual scanning electron micrograph of a metallorgraphic section of the material of FIG. 3 magnified 63.5 times, the surface of the specimen being at the lower right in the FIG.
Figure 5:
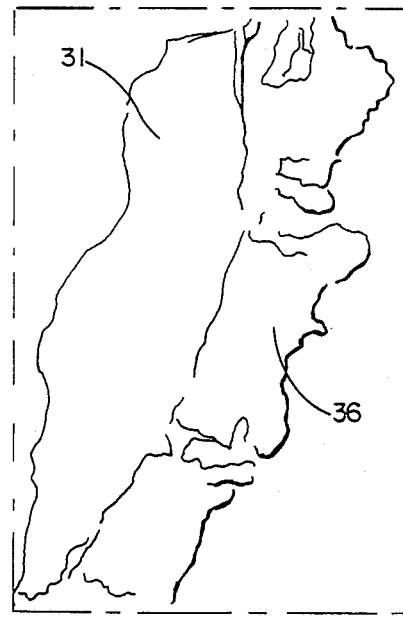
FIG. 5 is a draftsman's rendering of an actual photograph of a section as in FIG. 4, but magnified 948 times and showing only a portion of one of the metal wires forming the porous surface and the coating of the wire.

A section of the mesh of 17 cut through and examined by scanning electron microscopy, is shown in FIG. 4. The surface of the mesh (the direction pointing out of the scanning electron micrograph in FIG. 3) is pointing to the lower right hand corner in FIG. 4. The scanning electron micrograph of the section is enlarged 63.5 times. The typical cut sections of the wires are shown as at 31 and 32. The elongations of the wire sections as at 32 is due to the fact that the plane of the cut is at an oblique angle to the wire diameter. Apparent loose particles, as at 33, are not actually loose but merely represent a particle that is connected out of the plane of the section. The surfaces 34, 35, 37 of the wires are coated with the α-tricalcium phosphate 33, 36, and 38. In the embodiment shown the maximum coating thickness is approximately 30 microns with an average thickness of 20 microns on the exterior surfaces, such as 37, of the outer wires of the mesh. The coating intrudes approximately 0.020 inches (500 microns) into the mesh with the continuity of the coating decreasing from the outside toward the inside. FIG. 5 shows another view of the embodiment of FIG. 4, except magnified to 948 times.

The coated fiber metal parts shown in FIGS. 1, 3, 4, and 5 are made in the following manner. Commercially pure wire is formed into pads and is sintered into place on the prosthesis according to the process described in U.S. Pat. No. 3,906,550. The mesh is then plasma sprayed with a material that, after spraying and cooling, is bioabsorbable. Similarly, the coated parts 20 shown in FIG. 2 may be made by first plasma spraying the metal surface onto the base member (under surface 24), and then plasma spraying onto the resulting porous surface a coating of a substance which cools to a bioabsorbable material.

Metal cylinders were made according to the above-described process. The wire used was commercially pure titanium having a diameter of approximately 0.01 inches and was cut into about 1 inch lengths. The mesh had a thickness of approximately 2 mm and was sintered to a central titanium rod with a threaded portion to permit attachment to a mechanical testing device. The cylinders had a diameter of 9.5 mm and a length of 50 mm. The fiber mesh cylinders were then plasma sprayed with a material comprising approximately 50% hydroxyapatite and 50% β-tricalcium phosphate. The conventional plasma spraying process as described in U.S. Pat. No. 3,605,123 was used. Subsequent analysis of the plasma sprayed material by x-ray diffraction showed that the 50/50 hydroxyapatite β-tricalcium phosphate material had transformed to primarily α-tricalcium phosphate. Some β-tricalcium phosphate and hydroxyapatite remained. The diffraction data also showed some lines that have not yet been identified, but are thought to be a high temperature calcium phosphate. The diffraction line width indicated that the crystallite size was smaller than that in conventional ceramic.

The cylinders were implanted in canine femurs along with similar cylinders treated with a number of other materials that have been described as osteogenic in the literature, such as β-tricalcium phosphate, demineralized bone powder, and autogeneous bone and marrow. After lengths of time extending from two weeks to six weeks, the animals were sacrificed and the samples were pulled out of the femurs. The samples made by the technique according to the invention had the highest pull out strength. The high pull out strength is obviously indicative of the strongest fixation, and is generally considered in the art to be indicative of improved bony ingrowth. The samples made according to the invention were able to be handled according to normal procedures for packaging and implantation in the animals without degradation.

It is believed that the transformation of the hydroxyapatite/β-tricalcium phosphate material into α-tricalcium phosphate is due to the fact that the plasma spraying process provides transformation energy to the material. With this in view, other methods of applying the material which will provide energy for the transformation may be used to apply the coating, such as sputtering, electrophoresis, electrostatic spraying, etc.

Novel parts for implantation in the human body and the method for making the parts, which yield improved fixation and bony ingrowth, and which have numerous other features and advantages, have been described. While the above description of the invention has been referenced to a few particular embodiments, it is evident that, now that the advantage of coating a porous surface of a prosthesis with bioabsorbable material has been disclosed, those skilled in the art can now make numerous uses of and modifications of and departures from the specific embodiments described herein without departing from the inventive concepts. For example, the coated porous surface can be used in combination with many types of implantable fixators other than those described, as for example with knee prostheses, bone plates, intramedullary rods, etc. In addition, other bioabsorbable materials such as the calcium pyrophosphates or polylactic acids may be used. Similarly, other thicknesses than those specifically described may be also used. Similarly, the base member of the prosthesis and/or the porous layer may be made of metals, such as cobalt-chrome steel alloy, stainless steel, etc., and other materials suitable for implantation in bodies. It is clear that now that the principles of the invention have been disclosed, those skilled in the art can substitute numerous other equivalent parts. Consequently the invention is to be construed as embracing each and every novel feature and novel combination of features within the appended claims.

What we claim is:

1. A method of manufacturing a prosthetic part for use as a body implant comprising the steps of:
    providing a base member having a porous surface region on which bone attachment is desired;
    providing a coating material of hydroxyapatite and β-tricalcium phosphate; and
    applying said coating material directly to said porous surface region for adherence to said porous surface region, while providing energy sufficient to transform said coating material to a state in which it is bioabsorbable, said step of applying comprising heating said coating material to a temperature greater than 1350° and applying it to said porous surface region, said coating material upon receiving said provided energy during the application thereof transforms to primarily α-tricalcium phosphate on said porous surface region, and said coating material includes the α-tricalcium phosphate only after the application of the coating material to said porous surface region.

2. The method as described in claim 1 wherein said coating material intrudes into said porous surface region in decreasing continuity from the outside of said porous surface toward the inside of said porous surface.

* * * * *